United States Patent
Meyer et al.

(10) Patent No.: US 8,852,087 B2
(45) Date of Patent: Oct. 7, 2014

(54) ENDOSCOPE WITH VARIABLE DIRECTION OF VIEW

(75) Inventors: Andrea Meyer, Ratshausen (DE); Norbert Haeckl, Leibertingen (DE)

(73) Assignee: Henke-Sass, Wolf GmbH, Tuttlingen (DE)

(*) Notice: Subject to any disclaimer, the term of this patent is extended or adjusted under 35 U.S.C. 154(b) by 92 days.

(21) Appl. No.: 13/446,849

(22) Filed: Apr. 13, 2012

(65) Prior Publication Data

US 2012/0265017 A1    Oct. 18, 2012

(30) Foreign Application Priority Data

Apr. 15, 2011 (DE) .................. 10 2011 007 484

(51) Int. Cl.
*A61B 1/00* (2006.01)
*G02B 23/24* (2006.01)

(52) U.S. Cl.
CPC ......... *A61B 1/00183* (2013.01); *A61B 1/00066* (2013.01); *A61B 1/00096* (2013.01); *A61B 18/002* (2013.01); *G02B 23/2423* (2013.01); *A61B 1/00195* (2013.01)
USPC ............... 600/173; 600/171; 600/174

(58) Field of Classification Search
USPC ......... 600/107, 109–113, 127–130, 157, 160, 600/166–181
See application file for complete search history.

(56) References Cited

U.S. PATENT DOCUMENTS

| | | |
|---|---|---|
| 3,856,000 A | 12/1974 | Chikama |
| 6,364,830 B1 | 4/2002 | Durell |
| 6,537,210 B1 | 3/2003 | Wulfsberg |
| 6,560,013 B1 | 5/2003 | Ramsbottom |
| 2002/0022767 A1 | 2/2002 | Dohi et al. |
| 2008/0177138 A1* | 7/2008 | Courtney et al. ............ 600/109 |
| 2010/0022838 A1* | 1/2010 | Hoeg ............................ 600/131 |
| 2010/0030031 A1* | 2/2010 | Goldfarb et al. ............ 600/163 |
| 2010/0069712 A1* | 3/2010 | Yamaya ....................... 600/107 |
| 2012/0136213 A1* | 5/2012 | Weimer et al. .............. 600/173 |

FOREIGN PATENT DOCUMENTS

| | | |
|---|---|---|
| DE | 19927816 A1 | 1/2001 |
| DE | 102009049143 B3 | 12/2010 |
| EP | 1 056 388 B1 | 12/2004 |

* cited by examiner

*Primary Examiner* — Matthew J Kasztejna
*Assistant Examiner* — Ryan Henderson
(74) *Attorney, Agent, or Firm* — Skaar Ulbrich Macari, P.A.

(57) ABSTRACT

An endoscope includes a handle and a shaft connected thereto. Imaging optics are arranged in the shaft that image an object located in the direction of view of the imaging optics in front of the shaft as an image and which to set the desired direction of view. The imaging optics comprise a swivellably housed deflecting unit positioned at the distal end of the shaft facing away from the handle. The possible swivel range of the imaging optics has a first and a second limit, as well as an actuating element, which is attached to the handle and which is mechanically connected to the deflecting unit. Thereby the swivel position of the deflecting unit within the swivel range can be changed in order to set a desired direction of view. A first mechanical stop is provided against which the deflecting unit lies when the first limit is reached.

9 Claims, 6 Drawing Sheets

ENDOSCOPE WITH VARIABLE DIRECTION OF VIEW

PRIORITY

The present application claims priority to German Application No. 102011007484.8, filed Apr. 15, 2011, which is hereby incorporated by reference in its entirety.

FIELD

The present invention relates to an endoscope with a variable direction of view. Such endoscopes frequently have at the distal end of the endoscope shaft a swivellably housed deflecting unit as part of the imaging optics in order to set the desired direction of view by means of the swivel position of the deflecting unit.

BACKGROUND

Endoscopes with a variable direction of view frequently have at the distal end of the endoscope shaft a swivellably housed deflecting unit as part of the imaging optics in order to set the desired direction of view by means of the swivel position of the deflecting unit.

Generally, the endoscope is laid out for a possible swivel range of the deflecting unit with a first and a second limit with the result that optimal imaging conditions obtain with swivel positions within this range. However, these optimal imaging conditions no longer obtain if the upper or lower limit of the swivel range is passed. In this case, for example, disadvantageous shading effects, undesired scattered light, poorer-quality images etc., may occur. Because the mechanism for swivelling the deflecting unit may always have a certain play this can disadvantageously lead to poorer-quality imaging properties if the upper or lower limit of the swivel range is set as swivel position and is passed because of the play of the swivelling mechanism while the endoscope is being used.

SUMMARY

It is an object of certain embodiments of the invention to provide an endoscope with improved imaging that addresses the issues discussed above. The object is achieved by the various embodiments of the invention, including the features recited in the claims.

In certain embodiments, an endoscope comprises a first mechanical stop against which the deflecting unit lies when the first limit is reached, it is possible to prevent with certainty the first limit from being passed, even if, e.g. because of the play of the swivel mechanism, a swivel angle of the deflecting unit lying beyond the limit could occur. Preferably the endoscope includes a second mechanical stop against which the deflecting unit lies when the second limit is reached. It is thereby ensured that neither the first nor the second limit of the swivel range is passed in undesired manner. The imaging quality of the endoscope according to the invention can thus be ensured for all set swivel positions lying in the swivel range.

The first or second stop can be designed at a mount of an optical element, adjacent to the deflecting unit, of the imaging optics. This is preferably the mount of the optical element, directly adjacent to the deflecting unit, of the imaging optics.

With the endoscope according to certain embodiments of the invention, a sliding element, the proximal end of which is connected to the actuating element, can be arranged displaceable in the endoscope shaft, wherein an actuation of the actuating element leads to a displacement of the sliding element and the second or first stop is designed at the distal end of the sliding element. In this way the second or first stop can be provided, in space-saving manner, as the distal end of the sliding element is used for this purpose. In particular the sliding element can be designed as a tube (and can thus also e.g. be called draw tube). This makes production of the endoscope easier.

Furthermore, the distal end of the sliding element can include a screening section, wherein the distal end of the sliding element is connected to the deflecting unit such that a displacement of the sliding element brings about a change in the swivel position of the deflecting unit and simultaneously a displacement of the screening section, in order to achieve, at the same time as setting the desired direction of view, a scattered-light screening for the area between the deflecting unit and an optical element, downstream of the deflecting unit, of the imaging optics. As the distal end of the sliding element has the screening section, the screening section and thus the shutter to suppress undesired scattered light is also positioned at the same time as the direction of view is set, with the result that the endoscope can be used without time delay when there is a change in the direction of view. In particular, it is not necessary to manually track the shutter position after setting a direction of view.

Preferably, to swivel the deflecting unit, the distal end of the sliding element engages in an area which does not lie on the swivel axis of the deflecting unit. Furthermore, to connect the distal end of the sliding element to the deflecting unit, an actuating pin can be provided as first connecting element and a receptacle guiding the actuating pin as second connecting element, wherein one of the two connecting elements is provided at the deflecting unit and the other of the two connecting elements at the sliding element. Preferably, the actuating pin is provided at the deflecting unit. The deflecting unit preferably has a deflecting element (e.g. a mirror or a prism) positioned in a holder. In this case the actuating pin is preferably provided at the holder.

With the endoscope according to certain embodiments of the invention, in each case one part of the holder can lie against the corresponding stop when the first and/or second limit is reached. Thus a mechanical stop is simply realized with which the first or second limit can be prevented from being passed in undesired manner. In particular, the sliding element can drive the deflecting unit such that there is an easily achievable mechanical solution in which, synchronously with setting the direction of view, the screening section is positioned to suppress scattered light.

The axis of rotation of the holder can preferably lie perpendicular to the longitudinal direction of the endoscope shaft. The holder can be rotated about its axis of rotation by means of the sliding element. For this, the proximal end of the sliding element can be moved axially by means of the actuating element. In particular, the actuating element can be mechanically connected to the sliding element via a first gear mechanism. The first gear mechanism can preferably be designed such that it converts a rotational movement of the actuating element into an axial movement of the sliding element.

The distal end of the sliding element having the screening section which forms a baffle which ensures, irrespective of the set swivel position of the holder of the deflecting element, that no undesired scattered light passes between the deflecting element or the deflecting unit and the downstream optical element in the imaging optics. For this, the distal end of the sliding element is preferably mechanically connected directly to the holder of the deflecting element.

With the endoscope according to certain embodiments of the invention, a first marking shutter can be provided which is mechanically connected to the actuating element such that it is moved synchronously with a change in the swivel position of the deflecting unit and displays the set direction of view by means of its visible position when observing the image. Thus the set direction of view can always be represented simply in the image. Therefore, when observing the image, a user can also always be provided visually with the information as to just which direction of view is set. The actuating element is preferably rotatably housed on the handle. In particular, it is housed rotatable about the longitudinal axis of the endoscope shaft. This makes it easier to operate the endoscope.

Furthermore, with the endoscope according to certain embodiments of the invention, the endoscope shaft can be rotatably housed on the handle and the endoscope can have a second marking shutter which is connected in rotation-resistant manner to the endoscope shaft and which, by means of its visual position when observing the image, displays the rotation position of the endoscope shaft. Thus the observer is advantageously visually provided with the direction of the view of the endoscope and also the rotation position of the endoscope shaft when he observes the image of the imaging optics.

In particular the set direction of view can be displayed via the position of the first marking shutter relative to the position of the second marking shutter when observing the image. Thus e.g. the angular separation between the two marking shutters can be varied in order to display the direction of view. In particular the angular separation between the two marking shutters can correspond to the set direction of view (for example relative to the longitudinal direction of the endoscope shaft). Thus it is very easy for the observer to see just which direction of view is set.

With the endoscope according to certain embodiments of the invention the actuating element can be connected to the first marking shutter via a reduction gear mechanism. Thus it is advantageously achieved that the movement (for example rotation) of the first marking shutter is smaller than the corresponding movement of the actuating element. The reduction gear mechanism can convert a rotation of the actuating element into an axial movement and the axial movement into a rotational movement of the first marking shutter. This can easily be produced mechanically with the desired precision. The first marking shutter is preferably positioned in the area of the field stop of the imaging optics. The second marking shutter can also preferably be positioned in the area of the field stop of the imaging stop. The first marking shutter is preferably housed rotatable relative to the imaging optics. In particular the first marking shutter can be designed on a rotatably housed sleeve which e.g. is arranged coaxially to the longitudinal direction or axis of the endoscope shaft.

The endoscope according to certain embodiments of the invention can be an endoscope with a rigid endoscope shaft. However, it is also possible that the endoscope shaft is designed such that at least sections of it can be bent out.

The distal end of the endoscope shaft can be sealed with a cover glass. In particular the distal end can be hermetically sealed, with the result that the endoscope shaft can be autoclaved.

The swivellable deflecting element is preferably a reflecting mirror or a reflecting prism.

Preferably a further illumination channel is provided in the endoscope shaft via which the object to be imaged can be illuminated. Illumination can take place for example by means of optical fibers which can be impacted by light at the handle. Naturally other types of illumination are also possible. In particular, a light source (e.g. one or more LED diodes) can be provided for illumination at the distal end of the endoscope shaft.

It is understood that the features mentioned above and those yet to be explained below can be used, not only in the stated combinations, but also in other combinations or alone, without departing from the scope of the present invention.

BRIEF DESCRIPTION OF THE DRAWINGS

The invention is explained in further detail below by way of example using the attached drawings which also disclose features essential to the invention.

DETAILED DESCRIPTION

In the following descriptions, the present invention will be explained with reference to example embodiments thereof. However, these example embodiments are not intended to limit the present invention to any specific example, environment, embodiment, applications or particular implementations described in these example embodiments. Therefore, descriptions of these example embodiments are only for purposes of illustration rather than limitation to the invention. It should be appreciated that in the following example embodiments and the attached drawings, elements unrelated to the present invention are omitted from depiction; and dimensional relationships among individual elements in the attached drawings are illustrated only for ease of understanding, but not to limit the actual scale.

Figure 1:
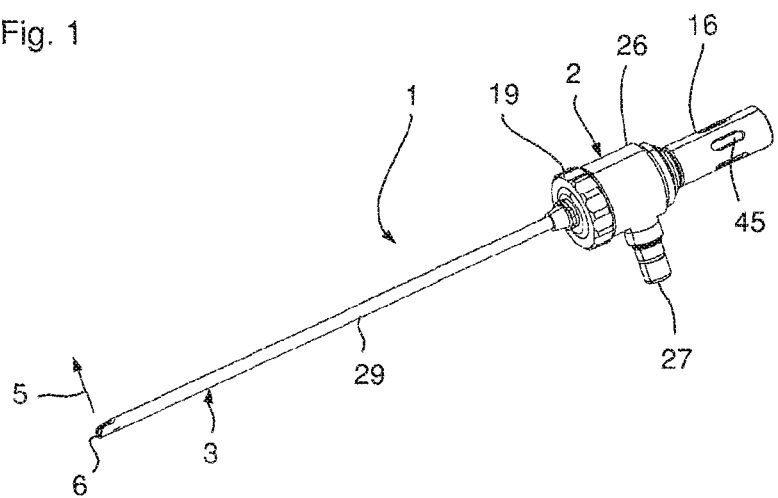
FIG. 1 is a schematic perspective representation of an embodiment of the endoscope according to the invention.

With the embodiment shown in FIG. 1 the endoscope 1 according to the invention with variable direction of view comprises a handle 2 and an endoscope shaft 3, the casing tube 29 of which can be seen in FIG. 1, connected to the handle 2.

Figure 2:
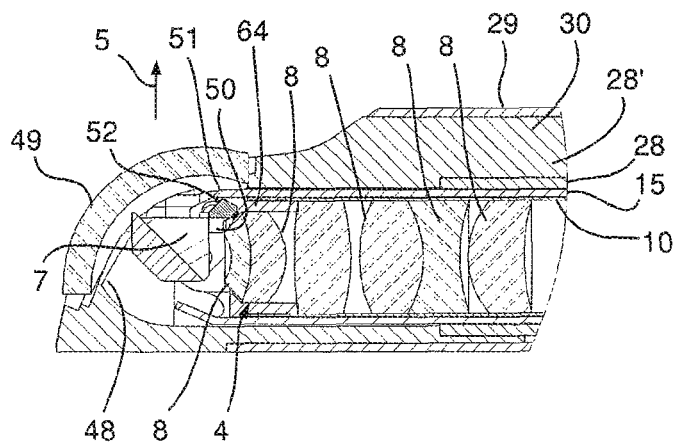
FIG. 2 is an enlarged sectional representation of the distal end of the endoscope shaft from FIG. 1.

As can be seen in particular from the enlarged sectional representation of the distal end 6 of the endoscope shaft 3 in FIG. 2, imaging optics 4 with which an object located in the direction of view 5 of the imaging optics 4 in front of the endoscope shaft 3 can be displayed as an image are arranged in the endoscope shaft 3.

The imaging optics 4 comprise a deflecting prism 7 as well as lenses 8 arranged downstream of this. The deflecting prism 7 sits in a prism holder 9 which is swivellably housed at the distal end of an optics tube 10 arranged in the endoscope shaft 3, as is best seen in the enlarged lateral view and top view of the distal end 6 of the endoscope shaft 3 in FIGS. 3 and 4 wherein, with the representations in FIGS. 3 and 4, in each case, the casing tube 29 is not drawn in.

Figure 3:
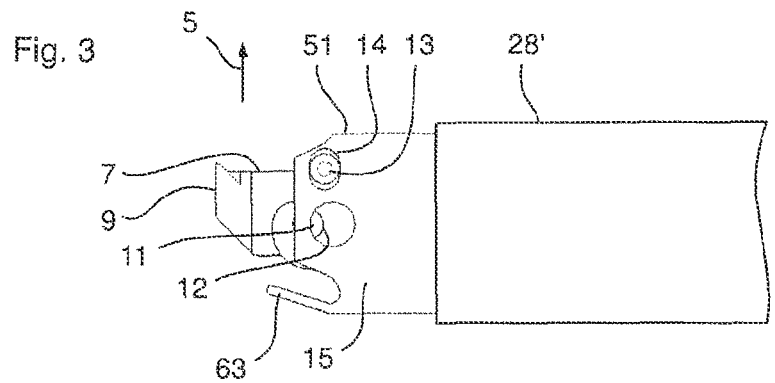
FIG. 3 is an enlarged lateral view of the distal end of the endoscope shaft with a first swivel position of the deflecting prism.

For the swivellable mounting, the prism holder 9 has two bearing pins 11 forming a swivel axis which sit in corresponding receptacles 12 of the distal end of the optics tube 10 (only a part of the left-hand bearing pin 11 as well as a part of the left-hand receptacle 12 can be seen in FIG. 3).

Figure 4:
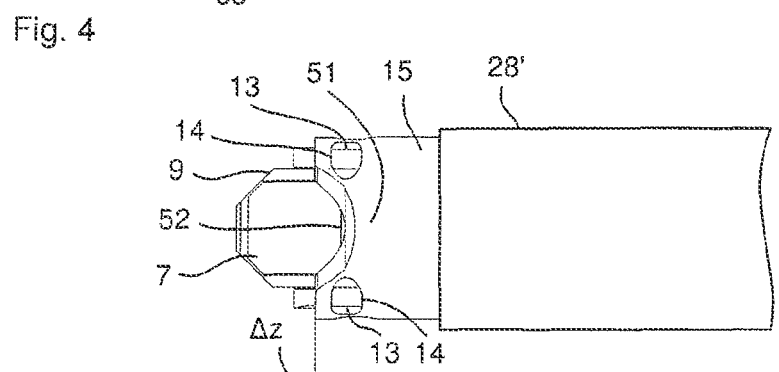
FIG. 4 is a top view of the distal end of the endoscope shaft according to FIG. 3.

The prism holder 9 also has two actuating pins 13 which sit in receptacles 14 of a draw tube 15 in which optics tube 10 is positioned, wherein, in the representations of FIGS. 3 and 4, the draw tube 15 almost completely covers the optics tube 10. The draw tube 15 is housed displaceable relative to the optics tube 10 and to the casing tube 29 in longitudinal direction of the endoscope shaft 3, wherein the axial position of the draw tube 15 can be set by means of an actuating element 16 (FIG. 1) attached to the handle 2, as is further described below in detail.

Figure 5:
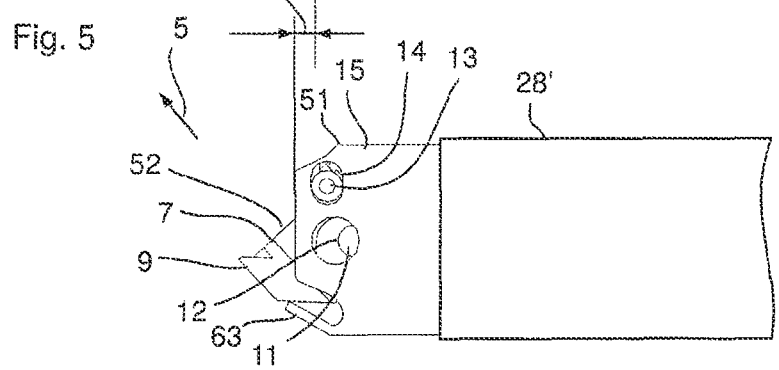
FIG. 5 is an enlarged lateral view of the distal end of the endoscope shaft with a second swivel position of the deflecting prism.
Figure 6:
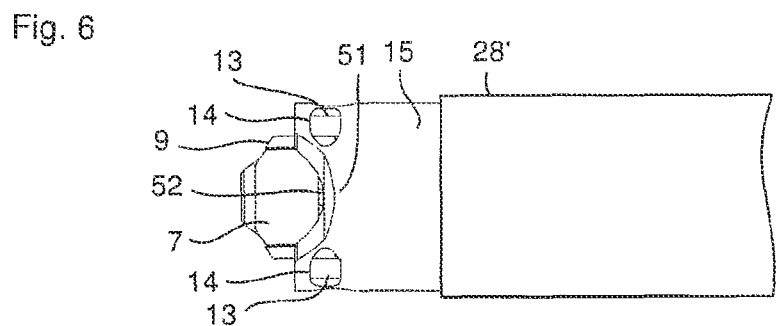
FIG. 6 is a top view of the distal end of the endoscope shaft according to FIG. 5.

The same views as in FIGS. 3 and 4 are shown in FIGS. 5 and 6, wherein however the draw tube 15 is axially displaced compared with FIGS. 3 and 4. The axial displacement is drawn in as Δz between FIGS. 4 and 5. As a comparison of the representations of FIGS. 3 and 4 with those of FIGS. 5 and 6 shows, an axial displacement of the draw tube 15 causes the actuating pins 13 to move around the bearing pins 11 at the distance from these predetermined by the design. The actuating pins 13 are thus moved on an orbit lying in the drawing plane of FIGS. 3 and 5, the centre of which is the bearing pins 11 and thus the point where the swivel axis pierces the drawing plane of FIGS. 3 and 5. This movement of the actuating pins 13 is possible as they are housed displaceable in the receptacles 14 of the distal end of the draw tube 15 (displaceable from top to bottom viewed in FIGS. 3 and 5).

Thus the axial displacement of the draw tube 15 leads to a swivelling of the prism holder 9 about the swivel axis defined by the bearing pins 11 which runs perpendicular to the drawing plane in FIGS. 3 and 5, and thus to a swivelling of the deflecting prism 7, whereby the direction of view 5 of the imaging optics 4 is changed. Thus the direction of view 5 in the representation from FIGS. 3 and 4 is approx. 90° (relative to the longitudinal direction of the endoscope shaft 3 which in each case lies in the drawing plane of FIGS. 3 to 6 and runs from left to right). In FIGS. 5 and 6 the direction of view 5 is, in contrast, approx. 45°.

The draw tube 15 or the distal end of the draw tube 15 is designed such that it serves simultaneously as movable baffle which with each swivel position of the deflecting prism 7 prevents with certainty undesired scattered light from reaching the area 50 (FIG. 2) between the prism holder 9 and the lenses 8 of the imaging optics 4, which would lead to an undesired impairment of the imaging quality of the imaging optics 4.

For this the draw tube 15 has a distal top screening section 51 which is always positioned directly above the rear part 52 of the prism holder 9, as is schematically represented in FIG. 2 and also in the different swivel positions according to FIGS. 3 to 6. It is thereby guaranteed that, irrespective of the set swivel position of the deflecting prism 7, no scattered light enters the area 50.

The draw tube 15 thus serves to screen the undesired scattered light and at the same time drives the deflecting prism 7 to set the desired swivel position and thus to set the desired direction of view 5. Thus, after setting a new swivel position the endoscope can be used without time delay, as the penetration of scattered light is always prevented with certainty. The imaging optics 4 are thus always shielded from direct scattered light irradiation.

Due to the swivelling or rotating, described in connection with FIGS. 3-6, of the deflecting prism 7, directions of view in the range of from approx. 10° and approx. 95° can be set. Thus the swivel positions of the reflecting prism 7 are, with regard to the directions of view of 10° and 95°, a first and second or a lower and an upper limit of the possible swivel range of the prism holder 9 and thus of the deflecting prism 7, for which the endoscope according to the invention is designed. Passing these limits (thus directions of view of <10° or directions of view of >95°) can lead, in undesired manner, to a poorer-quality image. This can, for example, be shown by an undesired trim in the displayed image, by scattered light, by poor illumination and/or generally poor imaging.

In order to prevent this, the endoscope according to the invention has a first and a second stop 61, 62, preventing the lower limit or the upper limit of the swivel range from being passed, respectively.

Figure 7:
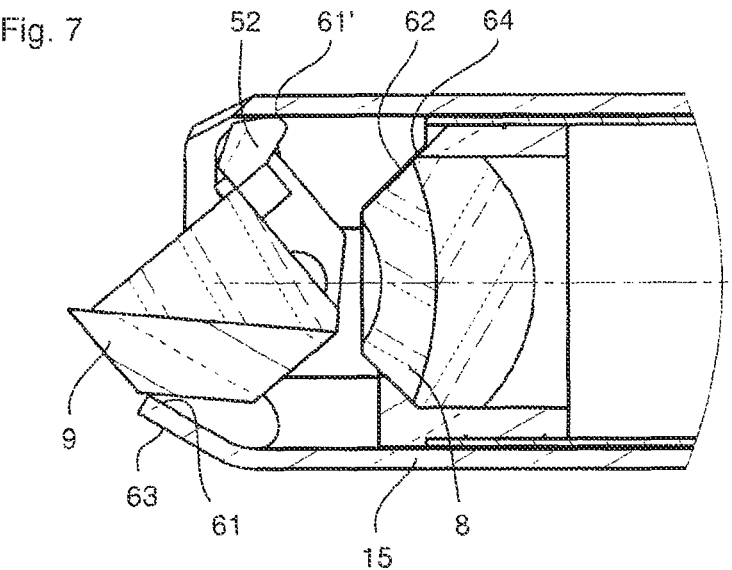
FIG. 7 is an enlarged sectional view of the distal end of the endoscope shaft according to FIG. 5.

The first stop 61 which is formed by the distal lower end area 63 of the draw tube 15 is shown in the sectional representation in FIG. 7. More precisely, the inside of the distal lower end area 63 serves as first stop against which the prism holder 9 lies, with the result that a further swivelling to smaller directions of view than the lower limit of approx. 10° here is prevented with certainty. Thus it can be prevented that the play in the swivelling mechanism does not lead, in undesired manner, to directions of view of less than approx. 10°. Thus it is ensured that the lower limit is not passed.

Furthermore, the rear part 52 of the prism holder 9 can, additionally (as shown in FIG. 7) or alternatively, be designed such that it lies, with a direction of view of approx. 10°, against the inside of the top distal end of the draw tube 15, with the result that this area forms a further or respectively the first stop 61'.

Figure 8:
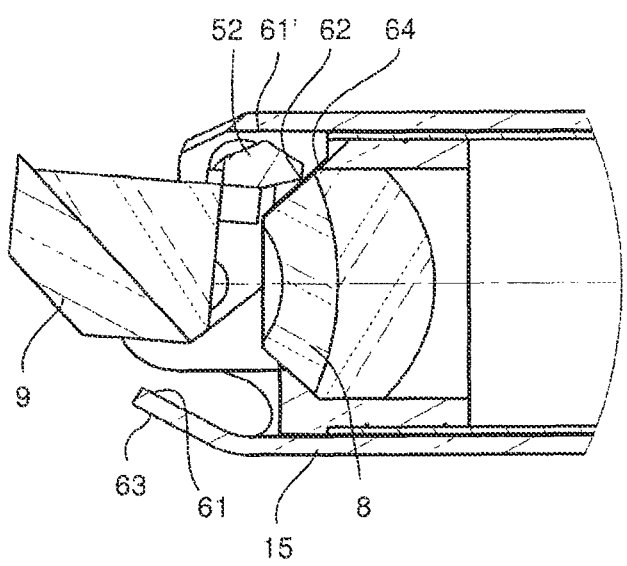
FIG. 8 is an enlarged sectional view of the distal end of the endoscope shaft according to FIG. 3.

As can be seen from the representation in FIG. 8, the mount 64 of the lens 8 which is directly adjacent to the deflecting prism 7 forms the second stop 62. Thus the rear part 52 of the prism holder 9 lies against the lens mount 64 in the area 62 with the result that a further swivelling of the prism holder 9 in the direction of even larger directions of view can be prevented with certainty.

With the endoscope according to the invention it is thus possible to prevent with certainty an passing of the limits of the provided swivel range. Swivel positions or angles of swivelling or of rotation of the prism holder 9 and thus of the prism 7 which would lead to directions of view which lie outside the predetermined range of the angle of view (here ≥10° and ≤95°), can therefore be prevented with certainty. Even the unavoidable play in the deflecting mechanism for the deflecting prism 7 does not therefore lead, disadvantageously, to the upper and/or lower limit of the swivel range being passed in undesired manner, which e.g. would lead to a poorer-quality imaging.

Naturally, the given range of the angle of view and the resulting swivel range is given by way of example. Thus the range of the angle of view can e.g. be 90°, 100°, 110°, 120° or 130°, wherein the lower limit is preferably 0° (thus a direction of view in the direction of the longitudinal axis of the endoscope shaft) and thus results in 90°, 100°, 110°, 120° or 130° for the upper limit. Naturally the lower limit can also have a value of less than 0°, such as e.g. −5° or −10°. For a lower limit of −5°, 85°, 95°, 105°, 115° or 125° result as upper limit for the given ranges of angle of view. Also, values of more than 0° for the lower limit, such as e.g. 5°, 10° or 15°, are possible. The specific fixing of the range of the angle of view and the lower and upper limit and thus the specific design of the endoscope is chosen depending on the respective case of application.

Figure 9:
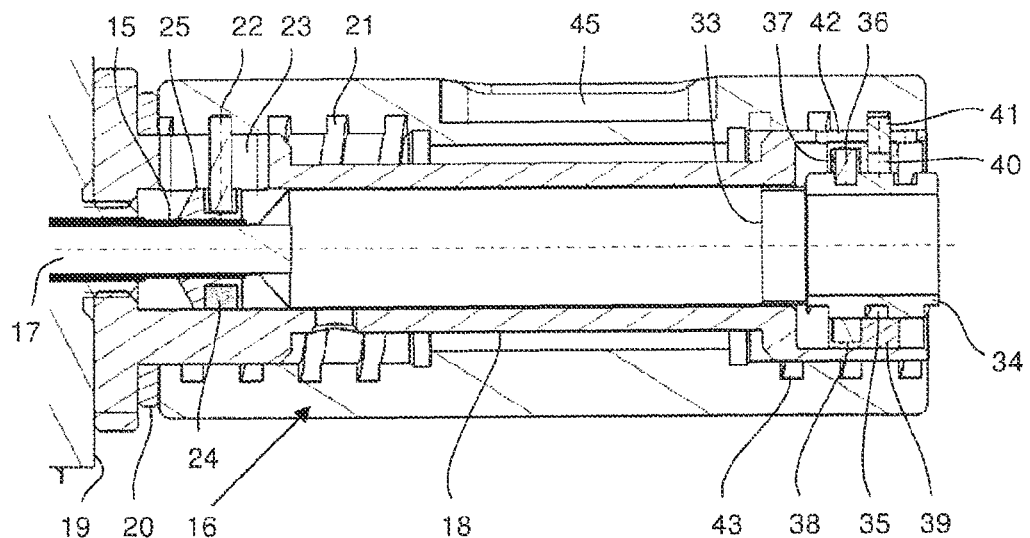
FIG. 9 is an enlarged sectional view of the proximal end of the handle of the endoscope according to FIG. 1.

The imaging optics 4 also have an image-transmission system (here in the form of rod lenses, one of which can be seen in the enlarged sectional representation of the proximal section of the handle 2 in FIG. 9) in the endoscope shaft 3 and in the handle 2 which serves to transmit the recorded image up to the proximal end of the handle where it is then made available. The image made available can be observed directly or via a proximally arranged eyepiece. It is also possible to attach for example a video camera which records the image and can display it via an output device (for example a monitor) to the proximal end of the handle 2.

As can be seen from the enlarged sectional representation of the proximal section of the handle 2 in FIG. 9, the actuating element 16 is designed in the form of a sleeve and rotatably housed on a guide sleeve 18 which for its part is connected in rotation-resistant manner to a main part 19 of the handle 2. A sliding disk 20 is provided between the distal end of the actuating element 16 and the guide sleeve 18.

On its inside, the actuating element 16 has in the distal area a first helical groove 21 into which the top end of a first bolt 22 projects. The first bolt 22 extends through a first oblong hole 23 extending in longitudinal direction of the endoscope shaft 3 (and thus from right to left in FIG. 9) of the guide sleeve 18 and is fixed at its bottom via a first Teflon ring 24 in a connecting part 25 which is connected in rotation-resistant manner to the proximal end of the draw tube 15.

Because of this structure, a rotation of the actuating element 16 about the longitudinal axis of the endoscope and relative to the main part 19 leads to the first bolt 22 being moved in axial direction (due to being guided through the first oblong hole 23 in the guide sleeve 18 connected in rotation-resistant manner to the main part 19), with the result that the connecting part 25 and thus the draw tube 15 are axially displaced. At the distal end of the draw tube 15 this displacement leads, as is represented in FIGS. 3 to 6, to a desired swivel position of the deflecting prism 7 being set.

The handle 2 also comprises a middle part 26 with an optical-fibre connection 27 (FIG. 1). The middle section 26 is connected to the endoscope shaft 3 in rotation-resistant manner and can be rotated about the longitudinal axis of the endoscope shaft 3 relative to the main part 19. For this, the endoscope shaft 3 is rotatably guided in the main part 19.

The endoscope shaft 3 also comprises as can best be seen from FIG. 2 an inner tube 28 with a distal end-piece 28' in which the draw tube 15, the optics tube 10 and the imaging optics 4 are arranged, and the casing tube 29, in which the inner tube 28 including distal end-piece 28' is inserted. The inner diameter of the casing tube 29 is larger than the outer diameter of the inner tube 28, with the result that there is a space 30 extending along the longitudinal direction of the endoscope shaft 3 between the two tubes 28 and 29. Optical fibers (not shown in FIG. 2) which serve to illuminate the object to be imaged are arranged in the space 30. The optical fibers can be impacted by light via the optical-fibre connection 27 at the middle part 26. The distal end-piece 28' has a distal opening 48 which is closed (preferably hermetically sealed) by means of a glass cover 49, with the result that the imaging optics 4 are protected against dirt.

Figure 10:
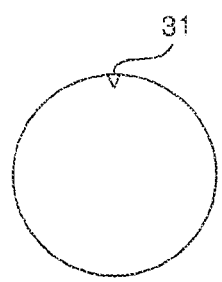
FIGS. 10 and 11 are representations explaining the fixed marking shutter.
Figure 11:
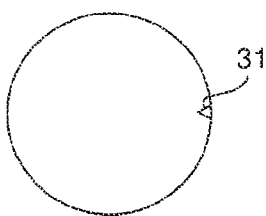

In order that the user can optically detect the rotation position of the endoscope shaft, when he observes the image produced by the imaging optics 4, a fixed marking sleeve 33 with a fixed marking shutter 31 is connected in rotation-resistant manner to the optics tube 10 at the proximal end of the optics tube (FIG. 9). Here, the fixed marking shutter 31 has the form of a triangle, as schematically represented in FIG. 10. If the user rotates the endoscope shaft 90° to the right (by rotating the middle part 26 relative to the main part 19), the fixed marking sleeve 33 moves and thus the fixed marking shutter 31 with it, with the result that the user sees the marking shutter in the position shown in FIG. 11 together with the image.

Figure 12:
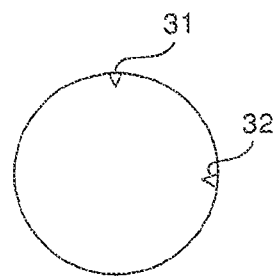
FIGS. 12 and 13 are representations explaining the fixed and rotatable marking shutter.
Figure 13:
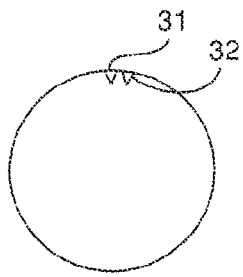

However, in the embodiment described here of the endoscope according to the invention, not only is a fixed marking shutter 31 provided but also a further rotatable marking shutter 32, which further displays in the image the direction of view 5 of the imaging optics 4 and thus the swivel position of the deflecting prism 7. The rotatable marking shutter 32 can have the same form (for example triangular form) as the fixed marking shutter 31, as shown schematically in FIG. 12. The case is shown in FIG. 12 where the swivel position of the prism corresponds to approx. 95°. If the swivel position shown in FIGS. 5 and 6 is set (direction of view of approx. 10°), the position of the rotatable marking shutter 32 changes relative to the fixed marking shutter 31 as represented in FIG. 13. Thus, when observing the image via the angle of rotation between both marking shutters 31 and 32, the user sees the set swivel position of the deflecting prism and therefore the set direction of view 5. Naturally, the two marking shutters 31 and 32 are preferably designed such that they can be distinguished clearly. Thus the two marking shutters 31 and 32 can have different colours. Additionally, or alternatively, the two marking shutters 31, 32 can have different forms.

Figure 14:
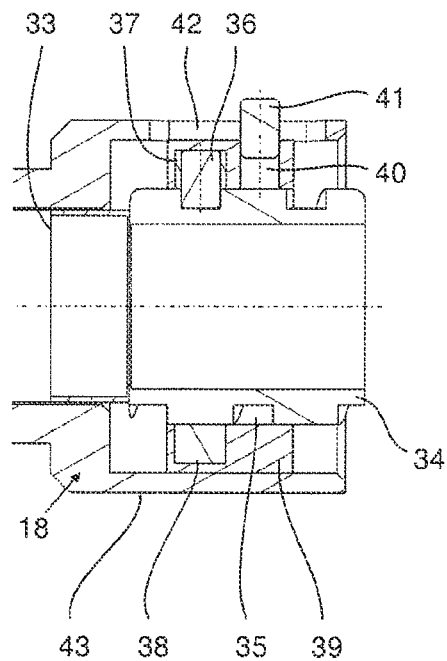
FIG. 14 is an enlarged sectional representation of the right-hand section of FIG. 9 without actuating element.

The rotatable marking shutter 32 is secured on the inside of a rotatable marking sleeve 34 (FIG. 9) such that it lies in the field of vision of the represented image. The rotatable marking sleeve 34 has on its outside a helical groove 35 into which a first pin 36 projects, as can be seen from FIG. 9 as well as from the enlarged detailed representation in FIG. 14.

The first pin 36 is firmly connected to a Teflon ring 37 which sits rotatable in an annular inner groove 38 of a sliding sleeve 39. The sliding sleeve 39 has a bore 40, axially spaced apart from the inner groove 38, in which a second pin 41 sits which projects through a second oblong hole 42 which extends in longitudinal direction of the endoscope shaft 3 of the guide sleeve 18. The top end of the second pin 41 opens into a groove 43 which is designed on the inside of the actuating element 16 and extends helically in the proximal area of the actuating element 16.

Because of this structure a rotation of the actuating element 16 relative to the guiding sleeve 18 leads to the rotational movement of the actuating element 16 being converted into an axial movement of the second pin 41 because of the second oblong hole 42. The axial movement of the second pin 41 leads to an axial movement of the sliding sleeve 39 which, because of the first pin 36, then leads to a rotational movement of the rotatable marking sleeve 34. Thus synchronously with the swivelling of the deflecting prism 7, because of a rotation of the actuating element 16, the rotatable marking sleeve 34 and thus the rotatable marking shutter 32 are rotated relative to the optics tube 10 and thus relative to the fixed marking shutter 31.

Figure 15:
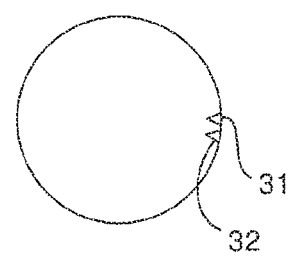
FIG. 15 is a representation explaining the fixed and rotatable marking shutter.

If the user rotates the endoscope shaft 3 90° to the right (by rotating the middle part 26 relative to the main part 19) compared with the position shown in FIG. 13, the draw tube 15 is thereby also rotated 90° to the right, whereby the actuating element 16 is also rotated to the right via the bolt 22. This leads to a rotation of the rotatable marking sleeve 34 90° to the right. As the fixed marking sleeve 33 is also rotated 90° to the right because of the rotation of the endoscope shaft 3, a user sees the two marking shutters 31, 32 in the position shown in FIG. 15 when observing the image. The user can thus immediately detect the rotation position of the endoscope shaft of 90° and the direction of view of 10°.

Figure 16:
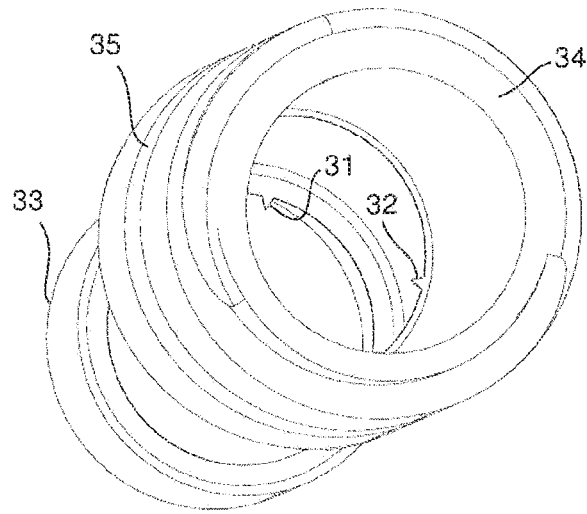
FIG. 16 is a perspective exploded representation of the two marking sleeves.

The two marking sleeves 33 and 34 are shown enlarged in FIG. 16 in a perspective exploded representation. The marking stops 31, 32 can be clearly seen in this representation.

The entire mechanism for rotating the rotatable marking shutter 32 is designed here as a reduction gear mechanism, with the result that a rotation of the actuating element 16 by a predetermined angle of rotation leads to a rotation of the rotatable marking shutter 32 in which the angle of rotation is smaller than the predetermined angle of rotation. The reduction gear mechanism structure is chosen here, as the necessary axial displacement of the draw tube 15 to swivel the deflecting prism 7 requires an angle of rotation of the actuating element 16 which is greater than the desired maximum angle of rotation of the rotatable marking shutter 32 or of the rotatable marking sleeve 34.

Thus it is possible to set the swivel position of the prism 7 very precisely, as a relatively large angle of rotation of the actuating element 16 is necessary in order to swivel the deflecting prism by a predetermined angle. Although the reduction gear mechanism is designed such that the angular separation between the two marking shutters 31 and 32 corresponds specifically to the angle of the set direction of view 5, a representation can nevertheless be achieved which is meaningful to the user.

The outside of the actuating element 16 can be ergonomically designed. Thus recesses 45 which guarantee a secure hold are visible in the representation of FIG. 1 and also in the representation of FIG. 9.

Figure 17:
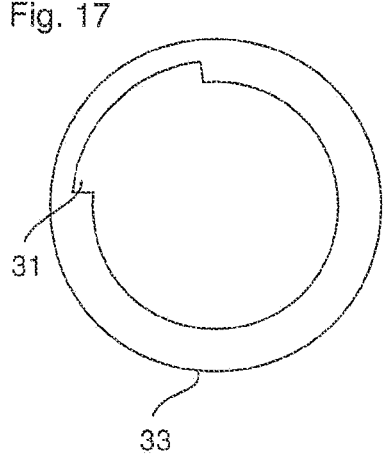
FIG. 17 is a schematic view of a variant of the fixed marking sleeve.
Figure 18:
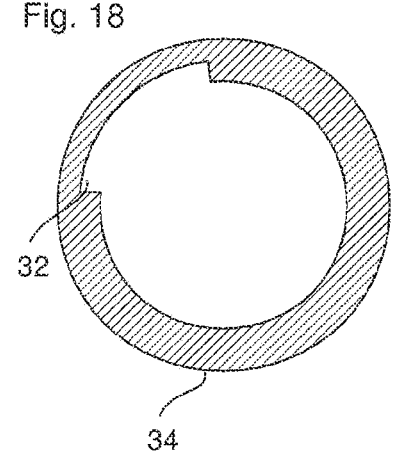
FIG. 18 is a schematic representation of a variant of the rotatable marking sleeve.
Figure 19:
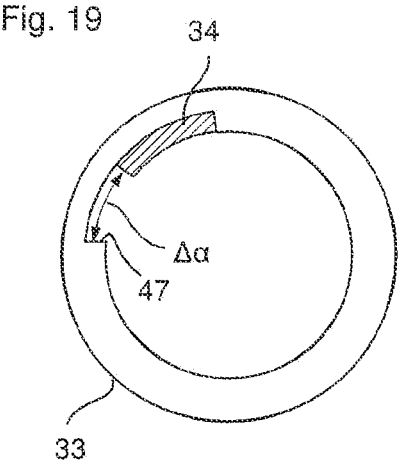
FIG. 19 is a schematic view explaining the type of representation of the two marking shutters when observing the imaging of the imaging optics.

As already mentioned, the marking shutters 31 and 32 can also have other forms. A top view of a variant of the fixed marking sleeve 33 is shown in FIG. 17. The ring-section-shaped recess serves as fixed marking shutter 31. In FIG. 18 a top view of a variant of the rotatable marking sleeve 34 is shown, wherein in the same way as with the fixed marking sleeve 33 the ring-section-shaped recess forms the rotatable marking shutter 32. In order to be able to distinguish between the two marking sleeves in the representation, the rotatable marking sleeve 34 is shaded. On the basis of the described arrangement of the two marking sleeves 33 and 34 a rotation of the rotatable marking sleeve 34 relative to the fixed marking sleeve 33 leads to the angular separation $\Delta\alpha$ between both ring-section-shaped recesses or between both marking shutters 31 and 32 changing (as is shown in FIG. 19). This angular separation $\Delta\alpha$ then shows the observer in turn the swivel position of the deflecting prism 7 in the image. The bottom edge 47 shows e.g. the rotation position of the endoscope shaft 3.

The above disclosure is related to the detailed technical contents and inventive features thereof. People skilled in this field may proceed with a variety of modifications and replacements based on the disclosures and suggestions of the invention as described without departing from the characteristics thereof. Nevertheless, although such modifications and replacements are not fully disclosed in the above descriptions, they have substantially been covered in the following claims as appended.

What is claimed is:

1. An Endoscope, comprising:
   a handle;
   an endoscope shaft connected to the handle;
   imaging optics arranged in the endoscope shaft which image an object located in a direction of view of the imaging optics in front of the endoscope shaft and is configured to set a desired direction of view comprise a pivotally housed deflecting unit which is positioned at a distal end of the endoscope shaft facing away from the handle and a possible swivel range of which has a first and a second limit; and
   an actuating element which is attached to the handle and which is mechanically connected to the deflecting unit and with which a swivel position of the deflecting unit within the swivel range can be changed in order to set the desired direction of view,
   wherein a first mechanical stop is provided against which the deflecting unit lies when the first limit is reached,
   wherein a sliding element, a proximal end of which is connected to the actuating element, is arranged displaceable in the endoscope shaft, wherein an actuation of the actuating element leads to a displacement of the sliding element and the first stop is formed integrally with a distal end of the sliding element,
   wherein the sliding element is formed as a tube, the imaging optics comprises the deflecting unit and lenses and the lenses are disposed within the tube,
   wherein, to connect the distal end of the sliding element to the deflecting unit an actuating pin is provided as first connecting element and a receptacle guiding the actuating pin as second connecting element, wherein one of the two connecting elements is provided at the deflecting unit and the other of the two connecting elements at the sliding element, and
   wherein during axial displacement of the sliding element the mating between the receptacle and the actuating pin causes the swivel position of the deflecting unit to change.

2. The Endoscope according to claim 1, wherein a second mechanical stop is provided against which the deflecting unit lies when the second limit is reached.

3. The Endoscope according to claim 2, wherein the first or second stop is formed at a mount of an optical element adjacent to the deflecting unit of the imaging optics.

4. The Endoscope according to claim 2, wherein the distal end of the sliding element has a screening section, wherein the distal end of the sliding element is connected to the deflecting unit such that a displacement of the sliding element brings about a change in the swivel position of the deflecting unit and simultaneously a displacement of the screening section, in order to achieve, at the same time as setting the desired direction of view, a scattered-light screening for an area between a deflecting unit and an optical element following deflection of the imaging optics.

5. The Endoscope according to claim 4, wherein, to swivel the deflecting unit, the distal end of the sliding element engages in an area which does not lie on a swivel axis of the deflecting unit.

6. The Endoscope according to claim 1, wherein the distal end of the sliding element has a screening section, wherein the distal end of the sliding element is connected to the deflecting unit such that a displacement of the sliding element brings about a change in the swivel position of the deflecting unit and simultaneously a displacement of the screening section, in order to achieve, at the same time as setting the desired direction of view, a scattered-light screening for an area between a deflecting unit and an optical element following deflection of the imaging optics.

7. The Endoscope according to claim 6, wherein, to swivel the deflecting unit, the distal end of the sliding element engages in an area which does not lie on a swivel axis of the deflecting unit.

8. The Endoscope according to claim 1, wherein a second mechanical stop is provided against which the deflecting unit lies when the second limit is reached, and wherein the deflecting unit includes a deflecting element fixed in a holder, wherein, when the first or second limit is reached, a part of the holder lies against a stop corresponding to the first limit or the second limit.

9. The Endoscope according to claim 8, wherein the deflecting element is formed as a prism.

\* \* \* \* \*